United States Patent
Georgakis et al.

(10) Patent No.: US 6,474,988 B1
(45) Date of Patent: Nov. 5, 2002

(54) HAND INSTRUMENT FOR DEBONDING ORTHODONTIC BRACKETS

(75) Inventors: Evangelos G. Georgakis, Alta Loma, CA (US); James D. Christoff, Birchwood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/702,595

(22) Filed: Oct. 31, 2000

Related U.S. Application Data (60) Provisional application No. 60/187,792, filed on Mar. 8, 2000.

(51) Int. Cl.[7] .................................................. A61C 7/00
(52) U.S. Cl. ....................................................... 433/4
(58) Field of Search ........................ 433/3, 4, 91, 157, 433/159, 116

(56) References Cited

U.S. PATENT DOCUMENTS

| | | | |
|---|---|---|---|
| 2,602,998 A | 7/1952 | Sprague | |
| 2,674,800 A | * 4/1954 | Osborn et al. | 433/159 |
| 3,755,902 A | 9/1973 | Northcutt | |
| 3,986,265 A | 10/1976 | Cusato | |
| 4,043,364 A | 8/1977 | Rose | |
| 4,155,164 A | 5/1979 | White | |
| 4,248,587 A | 2/1981 | Kurz | 433/4 |
| 4,249,060 A | 2/1981 | Colby | 433/24 |
| 4,360,341 A | 11/1982 | Dellinger | 433/24 |
| 4,486,177 A | 12/1984 | Lekawa | 433/161 |
| 4,551,096 A | 11/1985 | Dellinger | 433/24 |
| 4,553,932 A | 11/1985 | Armstrong et al. | 433/4 |
| 4,571,188 A | 2/1986 | Hamilton | 433/226 |
| 4,600,381 A | 7/1986 | Hodgson | 433/4 |
| 4,749,352 A | 6/1988 | Nicholson | 433/9 |
| 4,776,791 A | 10/1988 | Hannula et al. | 433/4 |
| 4,795,344 A | 1/1989 | Brewer et al. | 433/143 |
| 4,904,183 A | 2/1990 | Hannan et al. | 433/3 |
| 4,950,157 A | 8/1990 | Cleary | 433/4 |
| 4,952,142 A | 8/1990 | Nicholson | 433/9 |
| 4,954,080 A | 9/1990 | Kelly et al. | 433/8 |
| 5,044,954 A | * 9/1991 | Lukase et al. | 433/159 |
| 5,133,812 A | 7/1992 | Kelly et al. | 148/528 |
| 5,358,402 A | 10/1994 | Reed et al. | 433/8 |
| 5,366,372 A | 11/1994 | Hansen et al. | 433/4 |
| 5,380,196 A | 1/1995 | Kelly et al. | 433/8 |
| 5,439,379 A | 8/1995 | Hansen | 433/8 |
| 5,813,854 A | 9/1998 | Nikodem | 433/29 |
| 6,206,690 B1 | * 3/2001 | Vargas | 433/8 |

FOREIGN PATENT DOCUMENTS

FR     2 067 663     8/1971

\* cited by examiner

*Primary Examiner*—Cary E. O'Connor
(74) *Attorney, Agent, or Firm*—James D. Christoff (57) ABSTRACT

A hand instrument for debonding orthodontic brackets has a shield that extends around the bracket during a debonding procedure. In certain embodiments, the shield is connected to a vacuum source for carrying away any loose fragments or sections. In another embodiment, the debonding tool has at least one resilient surface for engagement with sides of the bracket to facilitate the application of uniform pressure on the bracket. Additional embodiments include a shield having at least one resilient outer edge for contact with the tooth surface.

71 Claims, 4 Drawing Sheets

HAND INSTRUMENT FOR DEBONDING ORTHODONTIC BRACKETS

This application claims priority to U.S. Provisional Patent Application No. 60/187,792, filed Mar. 8, 2000.

BACKGROUND OF THE INVENTION

1. Field of the Invention

This invention relates to a tool for use with orthodontic brackets that are directly secured to surfaces of teeth by an adhesive. More particularly, the present invention relates to a hand tool for detaching orthodontic brackets from teeth at the conclusion of treatment.

2. Description of the Related Art

Orthodontic treatment involves movement of the teeth toward positions for correct occlusion. During treatment, tiny orthodontic appliances known as brackets are connected to the teeth, and an archwire is placed in a slot of each bracket. The archwire forms a track to guide movement of the teeth to orthodontically correct positions.

Orthodontic brackets are typically made of metal, ceramic or plastic. Metal brackets are widely used and are considered by many orthodontists to have mechanical properties that are satisfactory for moving the teeth to desired positions. Unfortunately, metal brackets are not aesthetic in the mouth and often lead to comments of a "metallic mouth appearance" that can be an embarrassment to the patient.

Orthodontic brackets that are made of a plastic material are generally considered more aesthetic than metal brackets. However, some plastic brackets are stained by certain food and beverages and turn an unsightly color after a period of time. Moreover, the plastic material may slowly creep in use such that the archwire slot widens during a period of extended use and precise control of tooth movement is hindered.

Orthodontic brackets that are made of transparent or translucent ceramic materials overcome many of the problems associated with plastic brackets, since ceramic material is resistant to staining and does not deform by creep as in the case with plastic brackets.

U.S. Pat. No. 4,954,080, assigned to the assignee of the present invention, describes a color-free ceramic bracket made of polycrystalline material with a translucency that permits the natural color of the tooth to diffusely show through the bracket. An improved translucent polycrystalline ceramic bracket having a metallic archwire slot liner to enhance sliding movement of the bracket on the archwire is described in pending U.S. Pat. Nos. 5,358,402 and 5,380,196, both of which are assigned to the assignee of the present invention.

Metal brackets are typically debonded by using a peeling or prying motion. U.S. Pat. Nos. 3,986,265 and 4,248,587 describe plier-type hand instruments that are used with a prying action to remove orthodontic brackets. U.S. Pat. No. 4,553,932, assigned to the assignee of the present invention, describes a peeling-type debonding tool having a pull wire with a loop for hooking a wing of the bracket. The loop applies a pulling force to a tiewing located on an upper or lower portion of the bracket while a pair of spaced apart abutments engage the tooth on opposite sides of the bracket.

Peeling-type debonding methods are usually considered satisfactory for detaching brackets made of ductile materials such as metal. Debonding of such brackets often begins by fracturing the adhesive bond along one side of the bracket base, and then peeling or bending the base of the bracket so that the fracture propagates to remaining regions of the adhesive bond. In this manner, the debonding force is applied only to a relatively small, generally linear area at any particular point in time.

However, ceramic orthodontic brackets are relatively hard and brittle, and do not bend or flex like metal brackets during debonding. As a result, debonding occurs by fracturing the adhesive bond in all areas at essentially the same time, rather than in a propagating type of fracture as occurs when metal brackets are debonded by a peeling-type motion. Pulling on the tiewings of a ceramic bracket is not normally recommended because the ceramic material is brittle and the tiewings may break from remaining portions of the bracket.

Damage to the tooth structure may result during a debonding operation when excessive stress is applied to the tooth during attempts to lift or pry the bracket from the tooth. Tooth damage is more likely to occur when the tooth structure is weakened or has been previously damaged; however, such weakened or previously damaged tooth structure often cannot be noted by visual observation. Consequently, it is desirable that brackets are removed from the teeth with as little force as possible to minimize the risk of damage to the tooth.

It has been proposed in the past to weaken the strength of the bond between a ceramic bracket and the tooth so that debonding of the bracket is facilitated. However, such a solution is not entirely satisfactory because of the resulting increased likelihood that the bracket may unintentionally, prematurely debond during treatment. For example, a relatively weak adhesive may not have sufficient strength to resist debonding of the bracket when the bracket is subjected to relatively large forces, as when the patient bites into a relatively hard food object. In other instances, a bracket may debond due to forces exerted by the archwire, orthodontic auxiliaries or attachments coupled to the bracket. Premature debonding of orthodontic brackets represents a nuisance to both the orthodontist and the patient, since the detached bracket normally must be re-bonded or replaced with a new bracket in order for treatment to resume.

An improved ceramic bracket that overcomes the debonding problems mentioned above is described in U.S. Pat. Nos. 5,439,379 and 5,366,372. The ceramic brackets described in those references have a mesial section (i.e., a section facing toward the middle of the dental arch) and a distal section (i.e., a section facing away from the middle of the dental arch). The mesial and distal sections are spaced apart from each other by a channel that extends in a generally occlusal-gingival direction (i.e., a direction that extends from the outer tips of the teeth to the patient's gums or gingiva). The mesial and distal sections are connected to each other by a thin web of material that lies along the bottom of the channel.

The brackets that are described in U.S. Pat. Nos. 5,439,379 and 5,366,372 are debonded from the surface of the tooth at the conclusion of treatment by urging the mesial and distal sections in directions toward each other. As the sections pivot, the sections detach from underlying areas of the tooth. It is believed that such construction significantly lowers the stresses applied to the tooth surface in comparison to, for example, the stresses that are needed to debond a ceramic bracket of similar size by use of a tensile force in directions perpendicularly away from the tooth surface. As a consequence, the likelihood of injury to the enamel surface of the underlying tooth is reduced.

In certain embodiments of the brackets described in U.S. Pat. Nos. 5,439,379 and 5,366,372, a metallic archwire slot liner is fixed to the mesial and distal sections and enhances sliding motion of the brackets along the archwire. Advantageously, the archwire slot liner retains the sections together during and after a debonding operation to facilitate removing the bracket from the mouth as one coupled-together assembly.

However, brackets according to other embodiments described in U.S. Pat. Nos. 5,439,379 and 5,366,372 do not have a metallic archwire slot liner. As a consequence, it is possible for one of the sections in those embodiments to shift away from the other section and detach from the grip of the debonding tool during a debonding operation, especially in instances where the jaws of the debonding tool are not centrally located over the mesial and distal sides of the bracket. Additionally, if the practitioner uses excessive force on the handles of the debonding tool after the bracket has debonded it is possible for one or both of the sections to break into fragments that are expelled from the grip provided by the jaws of the debonding tool.

Unfortunately, it is undesirable for bracket sections and bracket fragments to become loose in the oral cavity. If such a situation occurs, debonding of the remaining brackets is often delayed while the sections or fragments in the oral cavity are retrieved. It can be difficult to find fragments that are of small size, especially when made of translucent or transparent material. Yet, such fragments should be retrieved so that they are not swallowed by the patient.

SUMMARY OF THE INVENTION

The present invention overcomes the problems noted above in connection with sections or fragments of brackets that become loose in the oral cavity during a debonding procedure. The invention involves a debonding tool having a shield that engages the tooth surface during a debonding procedure. In one embodiment, the shield has resilient edges for contact with the tooth to help provide a seal. In another embodiment, a vacuum source is connected to the shield for carrying away any loose fragments or section. In another embodiment, the debonding tool has at least one resilient pad located on one or both jaws of the tool to facilitate the application of equal forces in uniform manner over the entire area of the sides of the bracket in contact with the tool.

In more detail, the present invention is concerned in one aspect with a hand instrument for debonding an orthodontic bracket. The hand instrument includes a first jaw, a second jaw movable relative to the first jaw and a shield having a chamber. The first jaw and second jaw are located in the chamber. The shield has at least one outer, resilient edge for contact with the tooth surface.

Another aspect of the present invention is also directed toward a hand instrument for debonding an orthodontic bracket. In this aspect, the hand instrument includes a first jaw, a second jaw movable relative to the first jaw and a shield having a chamber. The first jaw and the second jaw are located in the chamber. The shield has an outlet port for connecting the chamber to a vacuum source.

In another embodiment, the present invention is also directed to a hand instrument for debonding an orthodontic bracket. The hand instrument includes a first jaw and a second jaw that is movable relative to the first jaw. The hand instrument also includes a shield having a first section, a second section and a chamber located between the first section and the second section. The first section is movable toward the second section to reduce the size of the chamber when the first jaw and the second jaw have been placed next to the orthodontic bracket.

Another embodiment of the invention is also directed toward a hand instrument for debonding an orthodontic bracket. In this embodiment, the hand instrument has a first jaw and a second jaw movable relative to the first jaw. At least one of the jaws includes a resilient surface for facilitating the application of uniform pressure to one or more sides of an orthodontic bracket during a debonding procedure.

An additional aspect of the invention is directed toward a method of debonding an orthodontic bracket. In this aspect, the method includes the act of providing a shield having at least one resilient edge, and moving the resilient edge into contact with a surface of the tooth. The method also includes the act of moving a pair of jaws toward opposite sides of the bracket in order to urge the sides in directions toward each other.

Another aspect of the present is also directed toward a method of debonding an orthodontic bracket. This method includes the act of providing a hand instrument with a pair of movable jaws, at least one of which has a resilient surface. Additionally, the method includes the act of placing the jaws over opposite sides of the bracket. The method also includes the act of moving the jaws toward the sides of the bracket such that at least one resilient surface engages the bracket as the sides of the bracket are urged together.

In another embodiment, the invention is also directed toward a method of debonding an orthodontic bracket. In this embodiment, the method comprises the acts of placing a shield around the bracket, and moving a pair of jaws toward opposite sides of the bracket in order to urge the sides together. The method further includes the act of applying a source of vacuum to a chamber within the shield in order to help prevent the loss of any bracket fragment in the oral cavity.

The present invention is also directed in another embodiment toward a method of debonding an orthodontic bracket. In this embodiment, the method includes the acts of placing jaws of a hand instrument next to mesial and distal sides of the bracket, and providing a shield having a mesial section and a distal section. The method further includes the acts of shifting at least one of the mesial section and the distal section toward the other and in a direction toward an adjacent side of the bracket. The method also includes the act of moving the jaws toward each other to engage the sides of the bracket and urge the sides in directions toward each other.

Additional details and aspects of the invention are set out in the description that follows and are illustrated in the accompanying drawings.

DETAILED DESCRIPTION OF THE PREFERRED EMBODIMENTS

Although the disclosure set out below is detailed in order to enable those skilled in the art to practice the invention, the embodiments disclosed herein are to be considered only examples of the invention which may be embodied in other specific structures as well.

An orthodontic hand instrument for debonding an orthodontic bracket from a tooth according to one embodiment of the invention is illustrated in FIGS. 1–4 and is broadly designated by the numeral 20. The hand instrument 20 has a first handle 22 and a second handle 24, and the handles 22, 24 are outwardly bowed in opposite directions.

The first handle 22 is integrally connected to a first jaw 26, and the second handle 24 is integrally connected to a second jaw 28. Additionally, the handles 22, 24 are coupled together by a pivot 30. As the handles 22, 24 are squeezed together, the jaws 26, 28 swing in respective, opposite arcs about the pivot 30 and move toward each other.

Figure 1:
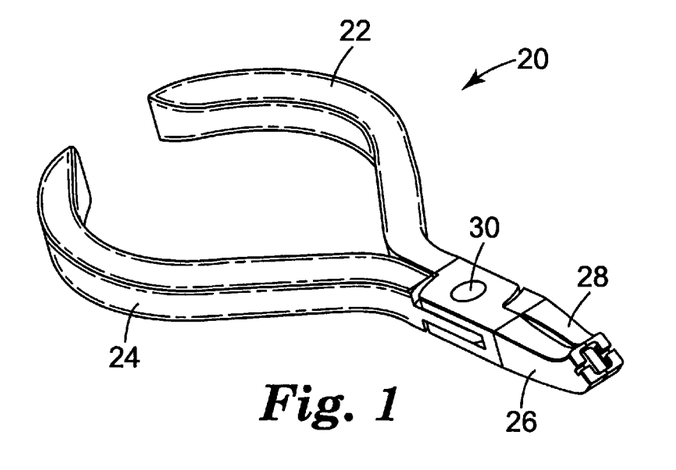
FIG. 1 is a perspective view of a hand instrument for debonding an orthodontic bracket according to one embodiment of the present invention.
Figure 2:
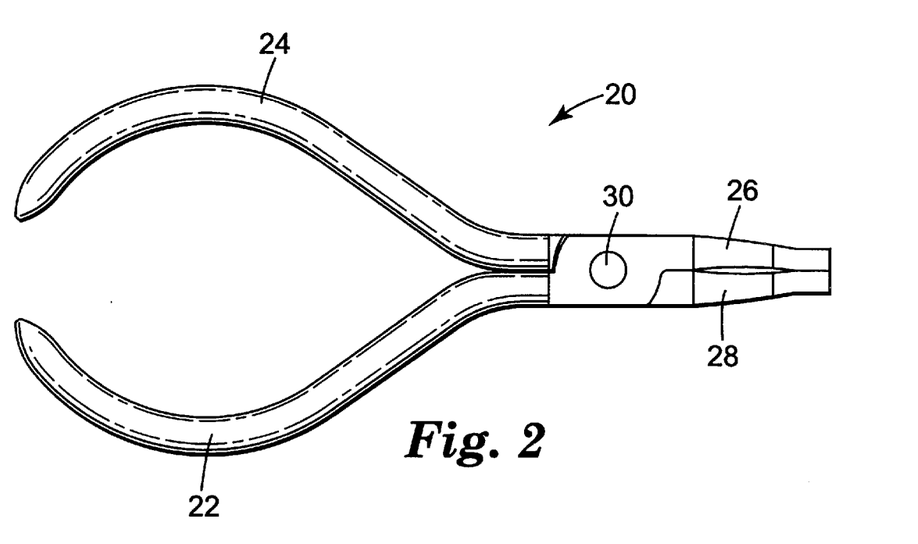
FIG. 2 is a side elevational view of the hand instrument shown in FIG. 1.
Figure 3:
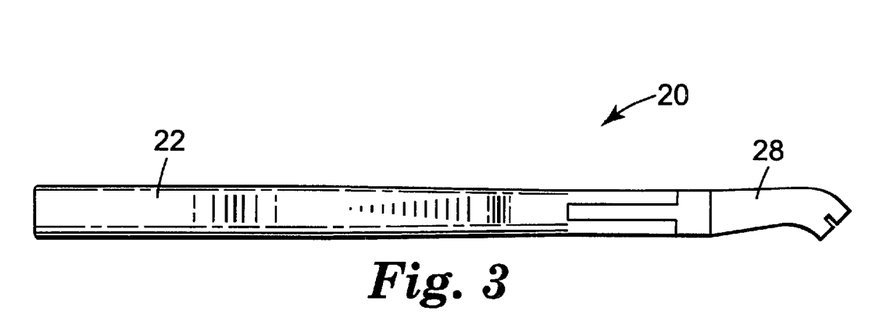
FIG. 3 is an elevational view showing another side of the hand instrument illustrated in FIGS. 1 and 2.
Figure 4:
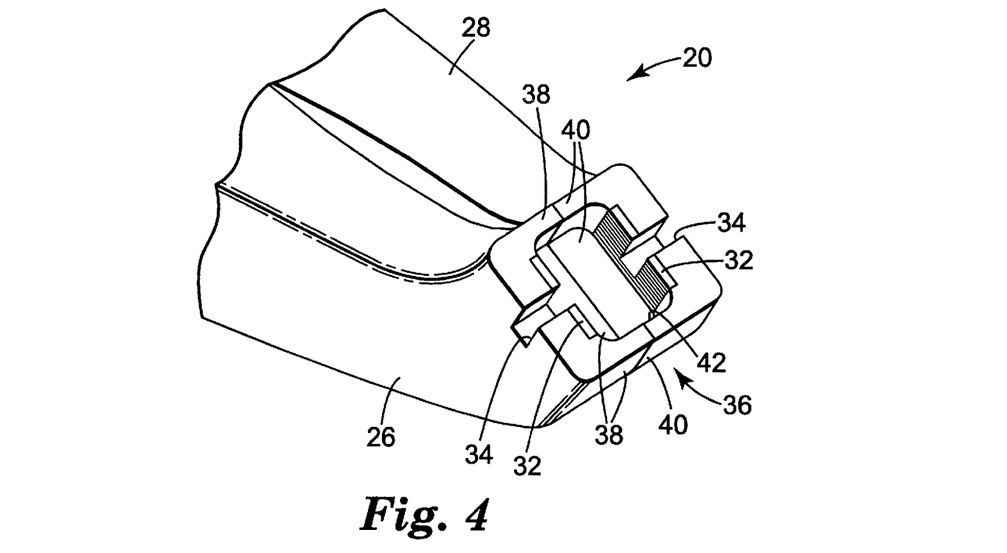
FIG. 4 is a fragmentary, enlarged, perspective view of a front portion of the hand instrument illustrated in FIGS. 1–3.

At least one of the jaws 26, 28 includes a resilient surface, and preferably a resilient pad, for engaging the sides of orthodontic brackets. In the embodiment shown in FIGS. 1–4, each of the jaws 26, 28 includes a resilient pad 32 having an inwardly-facing surface that is preferably provided with a series of grooves. The grooves enhance the grip of the jaws 26, 28 on the bracket during a debonding procedure. As shown in FIG. 4, the pads 32 face each other when the jaws 26, 28 are moved toward each other.

The pads 32 facilitates the application of a uniform force over the entire area of the sides of the bracket that is in contact with the jaws 26, 28. For example, if the hand instrument 20 is held in an orientation where the sides of the orthodontic bracket are not in precise, parallel relationship with the adjacent the pads 32, the pads 32 will help compensate by yielding in areas that are initially closer to the bracket. As the jaws 26, 28 move closer to the bracket in that situation, the pads 32 compress to matingly fit against the bracket, so that the force of the jaws 26, 28 tends to be more evenly distributed over the sides of the bracket. Such construction is an advantage, in that it increases the likelihood that the bracket will debond as intended.

Preferably, the pads 32 are made of a resilient, relatively soft material that can withstand repeated sterilization and/or disinfection procedures, and is also safe for use in the oral cavity. Examples of suitable materials for the pads 32 include urethanes and silicones. Optionally, the pads 32 may comprise a relatively thin coating of a resilient material such as pyrelene.

Preferably, the hand instrument 20 includes a pair of notches 34. In the embodiment shown in the drawings, the notches 34 extend through the pads 32 as well as through the jaws 26, 28, although other constructions are possible. The notches 34 enable the pads 32 and the jaws 26, 28 to be placed on opposite sides of an orthodontic bracket without removing the archwire from the bracket, so that the time needed for removing the archwire and the brackets at the conclusion of treatment can be reduced.

Preferably, the hand instrument 20 includes a shield 36 that extends over the bracket during a debonding operation. As shown in FIG. 4, the shield 36 in this embodiment includes three wall portions 38 that are integrally connected to the first jaw 26 and three wall portions 40 that are integrally connected to the second jaw 28. The wall portions 38, 40 extend across occlusal, gingival and labial sides of the bracket during a debonding procedure in order to help retain any sections or fragments of the bracket that might otherwise become loose in the oral cavity.

As shown in FIG. 4, the three wall portions 38 and the three wall portions 40 of the shield 36 cooperate with the pads 32 to provide a chamber 42 that substantially surrounds and encloses the bracket during a debonding procedure. Preferably, the wall portions 38 contact respective, opposed wall portions 40 as the jaws 26, 28 are closed and as the bracket is debonded, so that any bracket fragments will likely be captured within the chamber 42. Accordingly, the distance between the pads 32 should be substantially equal to the expected distance between the sides of the bracket immediately after debonding occurs. However, precise closure of the wall portions 38 against the wall portions 40 is not entirely necessary, and slight gaps may exist in instances where somewhat wider brackets are used.

Figure 5:
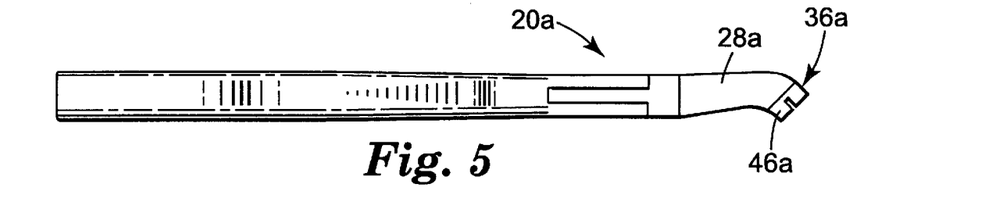
FIG. 5 is a side elevational view of a hand instrument for debonding an orthodontic bracket according to another embodiment of the invention.
Figure 6:
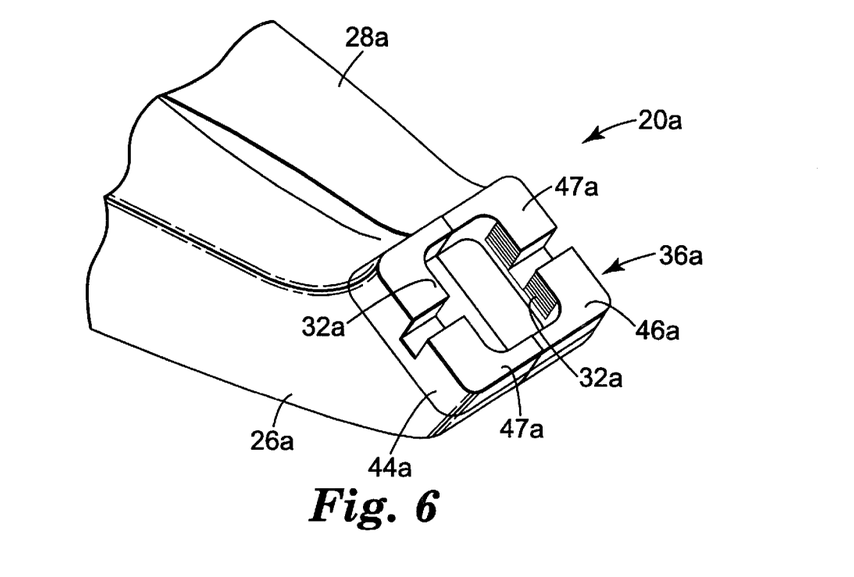
FIG. 6 is a fragmentary, enlarged, perspective view of a front portion of the hand instrument illustrated in FIGS. 5 and 6.

An orthodontic hand instrument 20a that is constructed in accordance with another embodiment of the invention is illustrated in FIGS. 5 and 6. Except as described below, the hand instrument 20a is identical to the hand instrument 20. Consequently, a detailed description of common elements and features need not be repeated.

The hand instrument 20a has a shield 36a that, in this instance, includes a first section 44a and a second section 46a. The first section 44a of the shield 36a is connected to a first jaw 26a, and preferably surrounds an outer tip of the first jaw 26a as best observed in FIG. 6. Similarly, the second section 46a of the shield 36a surrounds an outer tip of a second jaw 28a.

Preferably, the sections 44a, 46a are made of a relatively soft, resilient material. Each of the sections 44a, 46a includes an outer resilient edge 47a for contact with a surface of a tooth during a debonding procedure. The resilient outer edge 47a helps to establish a barrier or seal against the surface of the tooth, in order to facilitate the retention of any bracket fragments or sections that become loose during a debonding procedure.

Preferably, the hand instrument 20a also includes a pair of resilient pads 32a for engaging the sides of the bracket during debonding. In the illustrated embodiment, the pads 32a are integrally connected to the respective section 44a, 46a of the shield 36a. However, other constructions are also possible. For example, it may be desirable in certain instances to provide an outer edge for the shield 36a that is more resilient than the pads 32a.

The first and second shield 44a, 46a are preferably made of a resilient material that can withstand repeated sterilization and/or disinfection procedures. Examples of suitable materials for the shield sections 44a, 46a include urethanes and silicones. However, other materials are also possible.

The shield sections 44a, 46a are securely connected to the jaws 26a, 28a respectively so as not to inadvertently detach from the jaws 26a, 28a during debonding. For example, the sections 44a, 46a may be fixed to the jaws 26a, 28a respectively by means of an adhesive. As another option, the jaws 26a, 28a may be provided with grooves, undercuts or other features, and the shield sections 44a, 46a may be molded into or otherwise made to tightly and matingly engage such grooves, undercuts or other features so as to remain securely connected to the jaws 26a, 28a during the expected lifetime of the hand instrument 20a.

As another alternative, the shield sections 44a, 46a may be detachably connected to the jaws 26a, 28a respectively. In this alternative, the shield sections 44a, 46a may be disposed of after a single use, and optionally provided in a kit containing the orthodontic brackets. In this manner, the shield sections 44a, 46a and the pads 32a could be sized to precisely mate with the size of the brackets in the kits, so that the chamber established by the shield 36a is essentially closed as the pads 32a contact the bracket during debonding. In this alternative, the shield sections 44a, 46a may be releasably connected to the jaws 26a, 28a by a friction fit or other type of coupling, and subsequently pulled off of the jaws 26a, 28a before the remainder of the hand instrument 20a is sterilized.

Figure 7:
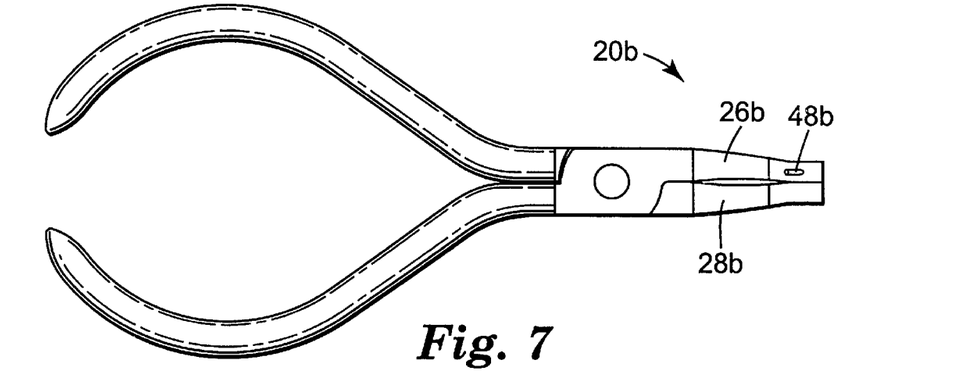
FIG. 7 is an elevational view of a hand instrument for debonding an orthodontic bracket that is constructed in accordance with a further embodiment of the invention.
Figure 8:
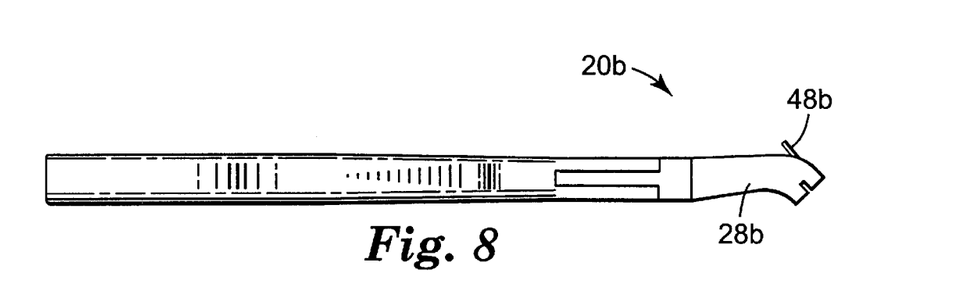
FIG. 8 is an elevational view showing another side of the hand instrument illustrated in FIG. 2.
Figure 9:
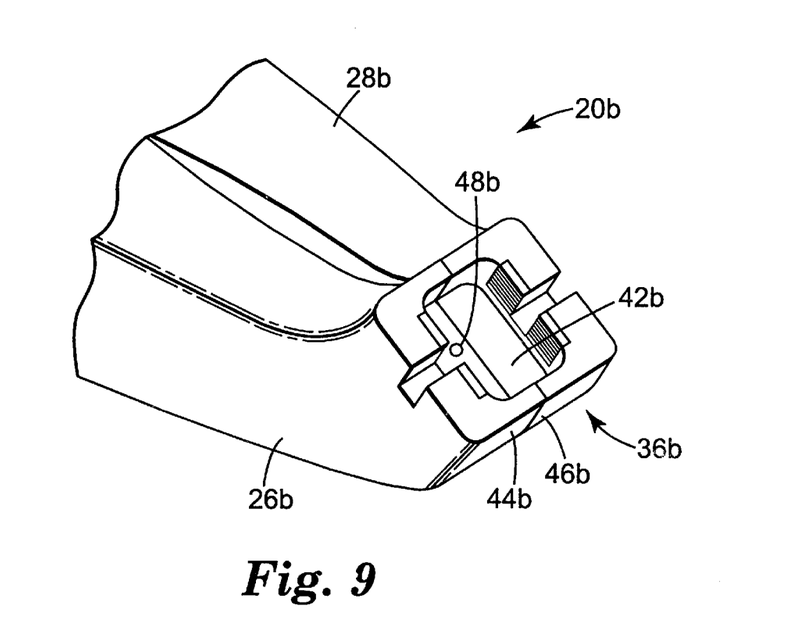
FIG. 9 is a fragmentary, enlarged, perspective view of a front portion of the hand instrument shown in FIGS. 7–8.

A hand instrument 20b for debonding an orthodontic bracket according to another embodiment of the invention is depicted in FIGS. 7–9. The hand instrument 20b is the same as the hand instrument 20 described above, with the exception of the differences noted below.

A shield 36b of the hand instrument 20b includes a first section 44b associated with a first jaw 26b and a second section 46b that is associated with the second jaw 28b. The shield 36b includes at least one outlet port for connection to a vacuum source. In the hand instrument 20b shown in the drawings, the shield 36b has a single outlet port 48b that extends through the first shield section 44b, although it should be understood in this regard that the outlet port may alternatively be connected to the second shield section 46b. As another option, two outlet ports could be provided, one for each of the shield sections 44b, 46b.

The outlet port 48b includes a fitting (see FIG. 8) that extends away from a chamber 42b for connection with flexible tubing that is also connected to the source of vacuum. The tubing is not shown in the drawings, but preferably is detachably connected to the fitting to facilitate sterilization of the hand instrument 20b. As an alternative to the embodiment shown, the outlet port could include a passageway that extends through the first jaw 26b and optionally through the first handle, in order to allow the tubing to be positioned further away from the bracket. In this manner, the practitioner's view of the debonding procedure may be enhanced.

The outlet port 48b and the vacuum source are an advantage, in that the negative air pressure can be utilized to sweep away any bracket fragments or bracket sections that become loose during a debonding procedure. For example, if the bracket is ceramic and if the hand instrument 20b loses its grip, any loose sections or fragments will tend to be drawn into the air stream provided by the source of vacuum. As a result, such fragments or sections will not drop into the oral cavity.

Preferably, the outlet port 48b and any tubing has a sufficiently large internal cross-sectional area to allow passage of the largest section or fragment of the bracket that is expected to become loose and be encountered during debonding. However, if the outlet port 48b is smaller in cross-sectional area than the largest bracket section or fragment that becomes loose, such fragment or section will tend to remain in the chamber 42b and near the outlet port 48b. In that instance, the practitioner can simply remove the hand instrument 20b from the oral cavity after debonding the bracket and remove any bracket fragment or section that is retained by the air stream near the outlet port 48b. Optionally, a screen or other mechanical retention device may be provided near the outlet port 48b to catch any fragments or sections.

Preferably, the vacuum source is the same source of negative air pressure that is. typically found in the offices of many orthodontic practitioners. The tubing described above is preferably provided with a detachable coupling at its end remote from the hand instrument 20b to readily connect to conventional vacuum sources in the orthodontic operatory. It is to be understood in this regard that "vacuum source" does not necessarily mean a source of absolute vacuum, but merely a source of air pressure that is below atmospheric pressure.

Figure 10:
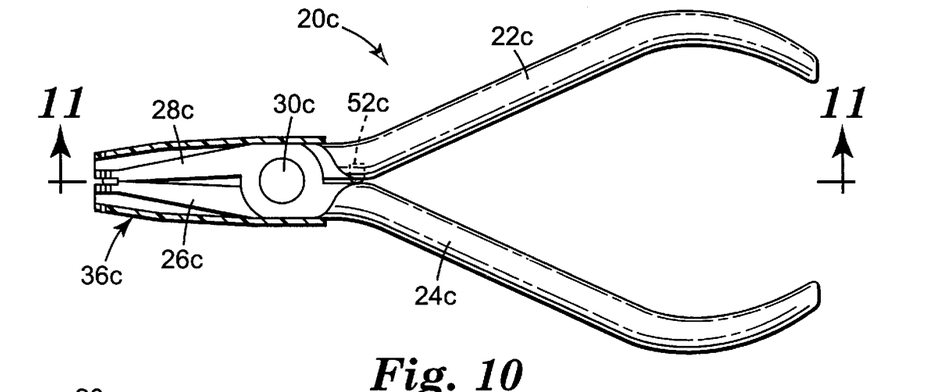
FIG. 10 is a side elevational view in partial section of a hand instrument for debonding an orthodontic bracket according to yet another embodiment of the invention.
Figure 11:
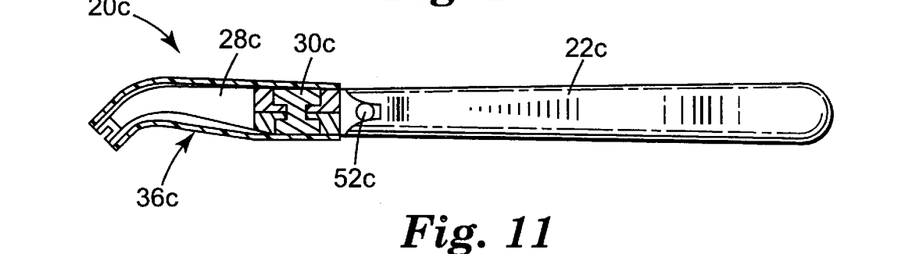
FIG. 11 is a side cross-sectional view of the hand instrument illustrated in FIG. 10, taken along lines 11—11 of FIG. 10.

A hand instrument 20c according to another embodiment of the invention is shown in FIGS. 10 and 11. The hand instrument 20c includes handles 22c, 24c that are connected together by a pivot 30c. The first handle 22c is integrally connected to a first jaw 26c, and the second handle 24c is integrally connected to a second jaw 28c.

Each of the jaws 26c, 28c includes an outer tip that is relatively narrow and has a generally rectangular cross-sectional area. Each of the outer tips of the jaws 26c, 28c has a notch similar to notch 34 for optionally receiving an archwire during a debonding operation.

The hand instrument 20c also includes a shield 36c that, in this instance, has a tubular configuration. The shield 36c is shown in cross-sectional view in FIGS. 10 and 11. Preferably, but not necessarily, the cross-sectional area of the shield 36c narrows as the outer tips of the jaws 26c, 28c are approached. However, the outer tip of the shield 36c is sufficiently large to enable the outer tips of the jaws 26c, 28c to open and fit over the sides of an orthodontic bracket.

Optionally, the shield 36c is detachably connected to the jaws 26c, 28c. In this instance, the shield 36c could be made of an inexpensive material such as polypropylene, and detached after use with a single patient. As an additional option, the shield 36c may be provided in a kit of orthodontic brackets that is adapted to be used with a single patient.

The shield 36c, or at least the outer edge of the shield 36c, is resilient. As such, when the outer edge of the shield 36c contacts the tooth, the shield 36c tends to establish a seal against the tooth surface. Preferably, the shield 36c is made of a transparent material to facilitate viewing the debonding procedure.

Optionally, the shield 36c includes an outlet port for connection with a source of vacuum. As a result, any loose bracket fragments or sections can be retained and preferably swept away by the vacuum source. The outer edge of the shield 36c need not tightly engage the tooth surface, because the stream of air moving through the vacuum port will tend to draw away any loose fragments or sections that are near the surface of the tooth.

Optionally, the hand instrument 20c except for the shield 36c is identical or similar to conventional orthodontic debonding tools. As such, the costs of manufacture can be reduced. Moreover, the shield 36c could be supplied as a separate component for practitioners who already possess suitable debonding pliers.

Preferably, but not necessarily, the hand instrument 20c also includes a stop for limiting movement of the jaws 26c, 28c toward each other. In the embodiment shown in FIGS. 10 and 11, the hand instrument 20c has a stop 52c that is threaded into a mating bore of the handle 22c. The stop 52c is adjustable to any one of a number of different positions to limit movement of the handles 22c, 24c and thus the jaws 26c, 28c, toward each other.

Figure 12:
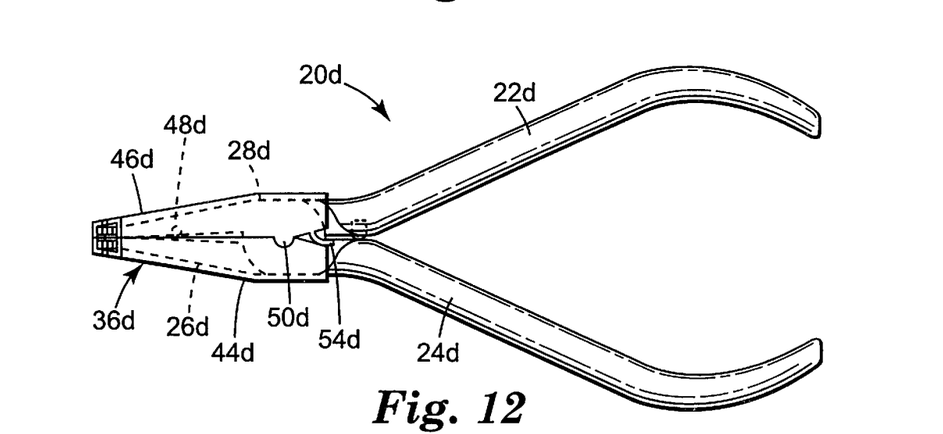
FIG. 12 is a side elevational view of a hand instrument for debonding an orthodontic bracket according to still another embodiment of the present invention.
Figure 13:
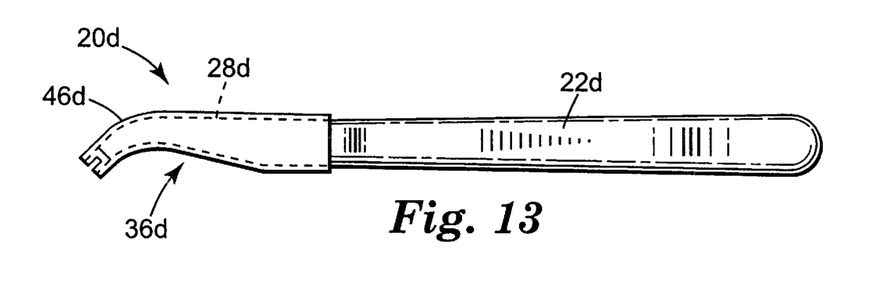
FIG. 13 is an elevational view of the hand instrument depicted in FIG. 12 but taken from another direction.

A hand instrument 20d for debonding orthodontic brackets according to another embodiment of the invention is illustrated in FIGS. 12 and 13. The hand instrument 20d is somewhat similar to the hand instrument 20c, except for the difference that are described below.

The hand instrument 20d has a shield 36d that includes a first section 44d and a second section 46d. The first section 44d extends over a first jaw 26d, and the second section 46d extends over a second jaw 28d. Preferably, the first shield section 44d is movable relative to the first jaw 26d, and the second shield section 46d is movable relative to the second jaw 28d, although other constructions are also possible.

The first shield section 44d and the second shield section 46d are connected to each other by a pivotal coupling 50d. The pivotal coupling 50d comprises a pair of tabs that are located on opposite sides of the second shield section 46d, each of which includes a inwardly extending pivot pin. Each pin in received in a hole of a similarly shaped tab that is integrally connected to the first shield section 44d.

The pivotal axis of the coupling 50d is parallel to, and preferably collinear with, the pivotal axis of a pivot (not shown, but similar to pivot 30c) that is connected to the jaws 26d, 28d. When the jaws 26d, 28d are moved away from each other by manipulation of handles 22d, 24d, the shield sections 44d, 46d pivot and also move away from each other at their outer tips.

Preferably, the shield 36d includes at least one spring element for urging the shield sections 44d, 46d toward each other and toward a closed position. In the illustrated embodiment, the shield 36d includes two spring elements 54d, one of which is illustrated in FIG. 12. The spring elements 54d are integrally connected to the second shield section 46d and are sufficiently resilient to urge the front portion of the shield sections 44d, 46d toward each other in an arc about the coupling 50d.

As a result, the shield sections 44d, 46d close and establish a chamber surrounding the bracket during a debonding procedure before such time as the jaws 26d, 28d move together sufficiently to debond the bracket from the tooth. However, the pivotal coupling 50d enables the shield sections 44d, 46d to be moved apart from each other when desired in instances where additional clearance is needed to place the shield 36d and the jaws 26d, 28d over the sides of an orthodontic bracket.

The shield 36d also includes an outlet port 48d for connection to a source of vacuum. In the embodiment shown in FIGS. 12 and 13, the outlet port 48d is connected to the first shield section 44d. Alternatively, the outlet port 48d may be connected to the second section 46d. As another option, two outlet ports may be provided, one for each of the shield sections 44d, 46d.

Preferably, the shield 36d including the sections 44d, 46d is made of a resilient, optically clear material. Optionally, the shield 36d may be detachably connected to remaining parts of the hand instrument 20d. It is also possible to provide an outer edge of the shield sections 44d, 46d with a layer of softer material for facilitating mating engagement with the tooth surface.

Those skilled in the art will recognize that a variety of modifications and additions may be made to the embodiments described and illustrated herein without departing from the gist of the invention. For example, the chamber in the various embodiments described above could have dimensions suitable for engaging a bracket that has a ligature extending around its tiewings. In that instance, the ligature would serve as a resilient cushion, such that the inwardly-facing pads of the jaws mentioned above could be eliminated. Optionally, each jaw could have a groove adjacent the notch that is sized and positioned to matingly engage the adjacent portion of the ligature.

Other embodiments are also possible. Accordingly, the invention should not be deemed limited to the specific embodiments that are described in detail above, but instead only by a fair scope of the claims that follow along with their equivalents.

What is claimed is:

1. A hand instrument for debonding an orthodontic bracket comprising:
    a first jaw;
    a second jaw movable relative to the first jaw; and
    a shield having a chamber, wherein the first jaw and the second jaw are located within the chamber, and wherein the shield has at least one outer, resilient edge for contact with a surface of the tooth.

2. A hand instrument according to claim 1 wherein the shield has a generally tubular configuration with a loop-shaped outer end portion that surrounds the jaws.

3. A hand instrument according to claim 1 wherein the shield has a first section and a second section, and wherein the first section is movable toward the second section to reduce the size of the chamber when the first jaw and the second jaw have been placed next to the orthodontic bracket.

4. A hand instrument according to claim 3 wherein the shield includes a pivotal connection for coupling the first section to the second section.

5. A hand instrument according to claim 4 wherein the hand instrument includes a pivot for coupling the first jaw to the second jaw, wherein the pivot has a central pivot axis, and wherein the pivotal connection of the shield has a central pivot axis that is generally parallel to the central pivot axis of the pivot.

6. A hand instrument according to claim 1 wherein at least one jaw includes a resilient surface for engaging the bracket.

7. A hand instrument according to claim 6 and including a notch extending through each resilient surface.

8. A hand instrument according to claim 1 wherein at least part of the shield is transparent.

9. A hand instrument according to claim 1 wherein the shield is detachably connected to the first jaw and the second jaw.

10. A hand instrument according to claim 1 wherein the shield is fixedly connected to the first jaw and the second jaw.

11. A hand instrument according to claim 1 and including a source of vacuum communicating with the chamber.

12. A hand instrument for debonding an orthodontic bracket comprising:
    a first jaw;
    a second jaw movable relative to the first jaw; and
    a shield having a chamber, wherein the first jaw and the second jaw are located in the chamber, and wherein the shield has an outlet port for connecting the chamber to a vacuum source.

13. A hand instrument according to claim 12 wherein the shield includes at least one outer, resilient edge for contact with a surface of the tooth.

14. A hand instrument according to claim 12 wherein the shield has a generally tubular configuration with a loop-shaped outer end portion that surrounds the jaws.

15. A hand instrument according to claim 12 wherein the shield includes a first section and a second section, and wherein the first section is movable toward the second section to reduce the size of the chamber when the first jaw and the second jaw have been placed next to the orthodontic bracket.

16. A hand instrument according to claim 15 wherein the shield includes at least one spring element for urging the first section toward the second section.

17. A hand instrument according to claim 15 wherein the shield includes a pivotal connection for coupling the first section to the second section.

18. A hand instrument according to claim 17 wherein the hand instrument has a pivot for coupling the first jaw to the second jaw, wherein the pivot has a central pivot axis, and wherein the pivotal connection of the shield has a central pivot axis that is generally parallel to the central pivot axis of the pivot.

19. A hand instrument according to claim 12 wherein at least one jaw includes a resilient surface for engaging the bracket.

20. A hand instrument according to claim 19 and including a notch extending through each resilient surface.

21. A hand instrument according to claim 12 wherein at least part of the shield is transparent.

22. A hand instrument according to claim 12 wherein the shield is detachably connected to the first jaw and the second jaw.

23. A hand instrument according to claim 12 wherein the shield is fixedly connected to the first jaw and the second jaw.

24. A hand instrument for debonding an orthodontic bracket comprising:
   a first jaw;
   a second jaw movable relative to the first jaw; and
   a shield having a first section, a second section and a chamber located between the first section and the second section, and wherein the first section is movable toward the second section to reduce the size of the chamber when the first jaw and the second jaw have been placed next to the orthodontic bracket.

25. A hand instrument according to claim 24 wherein the shield includes at least one spring element for urging the first section toward the second section.

26. A hand instrument according to claim 24 wherein the shield includes a pivotal connection for coupling the first section to the second section.

27. A hand instrument according to claim 26 wherein the hand instrument has a pivot for coupling the first jaw to the second jaw, wherein the pivot has a central pivot axis, and wherein the pivotal connection of the shield has a central pivot axis that is generally parallel to the central pivot axis of the pivot.

28. A hand instrument according to claim 27 wherein the central pivot axis of the pivotal connection is collinear to the central pivot axis of the pivot.

29. A hand instrument according to claim 24 wherein at least one jaw includes a resilient surface for engaging the bracket.

30. A hand instrument according to claim 29 and including a notch extending through each resilient surface.

31. A hand instrument according to claim 24 wherein the first section and the second section each include a resilient outer edge.

32. A hand instrument according to claim 24 wherein at least part of the shield is transparent.

33. A hand instrument for debonding an orthodontic bracket comprising:
   a first jaw;
   a second jaw movable relative to the first jaw, wherein at least one of the jaws includes a resilient surface for facilitating the application of uniform pressure to one or more sides of an orthodontic bracket during a debonding procedure; and
   a shield extending over the first jaw and the second jaw.

34. A hand instrument according to claim 33 wherein the shield has a generally tubular configuration with a loop-shaped outer end portion that surrounds the jaws.

35. A hand instrument according to claim 36 and including a notch extending through the resilient surface.

36. A hand instrument according to claim 33 wherein the shield includes at least one outer, resilient edge for contact with a surface of the tooth.

37. A hand instrument according to claim 33 wherein each resilient surface is part of a pad, and wherein each pad is integrally connected to the shield.

38. A hand instrument according to claim 37 wherein the shield is detachably connected to the first jaw and the second jaw.

39. A hand instrument according to claim 37 wherein the shield is fixedly connected to the first jaw and the second jaw.

40. A method of debonding an orthodontic bracket comprising the acts of:
   providing a hand instrument with a pair of movable jaws, at least one of which has a resilient outer edge;
   placing at least one resilient outer edge into contact with a surface of a tooth; and
   moving the jaws toward opposite sides of the bracket in order to urge the sides in directions toward each other.

41. A method of debonding an orthodontic bracket according to claim 40 and including the act of applying a source of vacuum in the vicinity of the bracket as the jaws are moved toward the sides of the bracket.

42. A method of debonding an orthodontic bracket according to claim 40 and including the act of placing a shield around the bracket.

43. A method of debonding an orthodontic bracket according to claim 40 and including the act of providing at least one of the jaws with a resilient surface for engaging the bracket.

44. A method of debonding an orthodontic bracket comprising the acts of:
   providing a hand instrument with a pair of movable jaws, at least one of which has a resilient surface;
   placing the jaws over opposite sides of the bracket; and
   moving the jaws toward the sides of the bracket such that at least one resilient surface engages the bracket as the sides of the bracket are urged together.

45. A method of debonding an orthodontic bracket according to claim 44 and including the act of applying a source of vacuum in the vicinity of the bracket as the jaws are moved toward the sides of the bracket.

46. A method of debonding an orthodontic bracket according to claim 44 and including the act of placing a shield over the bracket.

47. A method of debonding an orthodontic bracket according to claim 46 and including the act of providing the shield with one or more sections that are movable relative to at least one jaw toward the bracket.

48. A method of debonding an orthodontic bracket according to claim 46 and including the act of providing the shield with one or more transparent wall portions.

49. A method of debonding an orthodontic bracket according to claim 44 wherein the act of providing a hand instrument with a pair of movable jaws includes the act of providing both jaws with a resilient surface.

50. A method of debonding an orthodontic bracket according to claim 49 wherein the act of moving the jaws toward the sides of the bracket includes the act of engaging the resilient surface of each jaw with the bracket as the sides of the bracket are urged together.

51. A method of debonding an orthodontic bracket according to claim 44 wherein at least one resilient surface is part of a coating that extends over the jaw.

52. A method of debonding an orthodontic bracket according to claim 44 wherein the act of providing a hand instrument with a pair of movable jaws includes the act of providing at least one jaw with a notch.

53. A method of debonding an orthodontic bracket according to claim 44 wherein the act of providing a hand instrument with a pair of movable jaws includes the act of providing a notch that extends through at least one resilient surface.

54. A method of debonding an orthodontic bracket according to claim 44 wherein at least one resilient surface is provided with a series of grooves.

55. A method of debonding an orthodontic bracket according to claim 44 wherein at least one resilient surface is made of a material selected from the group of urethanes, silicones and pyrelenes.

56. A method of debonding an orthodontic bracket according to claim 44 wherein the act of placing the jaws over opposite sides of the bracket includes the act of placing at least one notch over an archwire connected to the bracket.

57. A method of debonding an orthodontic bracket according to claim 44 wherein the act of placing the jaws over opposite sides of the bracket is carried out by placing the jaws over mesial and distal sides of the bracket.

58. A method of debonding an orthodontic bracket comprising the acts of:
    placing a shield around the bracket;
    moving a pair of jaws toward opposite sides of the bracket in order to urge the sides together; and
    applying a source of vacuum to a chamber within the shield in order to help prevent the loss of any bracket fragments in the oral cavity.

59. A method of debonding an orthodontic bracket according to claim 58 wherein the act of moving a pair of jaws is carried out simultaneously with the act of applying a source of vacuum.

60. A method of debonding an orthodontic bracket according to claim 58 wherein the act of placing a shield around the bracket includes the act of moving sections of the shield toward each other.

61. A method of debonding an orthodontic bracket according to claim 58 wherein the act of placing a shield around the bracket includes the act of engaging the shield with the surface of the tooth.

62. A method of debonding an orthodontic bracket according to claim 61 wherein the act of engaging the shield with the surface of the tooth includes the act of contacting at least one resilient outer edge of the shield with the tooth.

63. A method of debonding an orthodontic bracket according to claim 58 and including the act of providing the shield with one or more transparent wall portions.

64. A method of debonding an orthodontic bracket according to claim 58 and including the act of providing at least one of the jaws with a resilient surface for engaging the bracket.

65. A method of debonding an orthodontic bracket comprising the acts of:
    placing jaws of a hand instrument next to mesial and distal sides of the bracket;
    providing a shield having a mesial section and a distal section;
    shifting at least one of the mesial section and the distal section toward the other and in a direction toward an adjacent side of the bracket; and
    moving the jaws toward each other to engage the sides of the bracket and urge the sides in directions toward each other.

66. A method of debonding an orthodontic bracket according to claim 65 wherein the act of moving the jaws toward each other is carried out simultaneously with the act of shifting at least one of the mesial section and the distal section toward each other.

67. A method of debonding an orthodontic bracket according to claim 65 wherein the act of moving the jaws toward each other is carried out subsequently to the act of shifting at least one of the mesial section and the distal section toward the other.

68. A method of debonding an orthodontic bracket according to claim 65 wherein the act of providing a shield includes the act of providing the shield with at least one transparent wall portion.

69. A method of debonding an orthodontic bracket according to claim 65 and including the act of contacting at least one outer, resilient edge of the shield with a surface of the tooth.

70. A method of debonding an orthodontic bracket according to claim 65 and including the act of applying a source of vacuum to one or more areas adjacent the bracket.

71. A method of debonding an orthodontic bracket according to claim 70 wherein the act of applying a source of vacuum includes the act of applying the source of vacuum to a chamber located between the mesial section and the distal section of the shield.

* * * * *

UNITED STATES PATENT AND TRADEMARK OFFICE
CERTIFICATE OF CORRECTION

PATENT NO.   : 6,474,988 B1                                                  Page 1 of 1
DATED        : November 5, 2002
INVENTOR(S)  : Georgakis, Evangelos G.

It is certified that error appears in the above-identified patent and that said Letters Patent is hereby corrected as shown below:

<u>Column 12,</u>
Line 15, delete "36" and insert in place thereof -- 33 --.

Signed and Sealed this

Ninth Day of September, 2003

JAMES E. ROGAN
*Director of the United States Patent and Trademark Office*